(12) United States Patent
Supersaxo et al.

(10) Patent No.: US 7,871,642 B2
(45) Date of Patent: *Jan. 18, 2011

(54) USE OF NANODISPERSIONS IN PHARMACEUTICAL END FORMULATIONS

(75) Inventors: Andreas Werner Supersaxo, Baar (CH); Hans Georg Weder, Rüschlikon (CH); Dietmar Hüglin, Weil am Rhein (DE); Joachim Friedrich Röding, Badenweiler (DE)

(73) Assignees: Ciba Specialty Chemicals Corporation, Tarrytown, NY (US); Vesifact AG, Baar (CH)

( * ) Notice: Subject to any disclaimer, the term of this patent is extended or adjusted under 35 U.S.C. 154(b) by 1209 days.

This patent is subject to a terminal disclaimer.

(21) Appl. No.: 11/446,844

(22) Filed: Jun. 5, 2006

(65) Prior Publication Data

US 2006/0292191 A1 Dec. 28, 2006

Related U.S. Application Data

(63) Continuation-in-part of application No. 09/306,006, filed on May 6, 1999, now Pat. No. 7,081,253.

(30) Foreign Application Priority Data

May 11, 1998 (EP) .................................. 98810422

(51) Int. Cl.
*A61K 9/127* (2006.01)
*A61K 9/107* (2006.01)

(52) U.S. Cl. ..................... 424/450; 424/401; 264/4.1; 264/4.3; 264/4.6; 514/937; 514/938

(58) Field of Classification Search .................. 424/450
See application file for complete search history.

(56) References Cited

U.S. PATENT DOCUMENTS

| | | | |
|---|---|---|---|
| 4,816,247 A | 3/1989 | Desai et al. | 424/80 |
| 4,874,850 A | 10/1989 | Paradies | 536/3 |
| 5,162,377 A | 11/1992 | Kakoki et al. | 514/772 |
| 5,190,936 A | 3/1993 | Laugier et al. | 514/169 |
| 5,338,761 A | 8/1994 | Nakajima et al. | 514/772 |
| 5,444,041 A | 8/1995 | Owen et al. | 514/2 |
| 5,472,706 A | 12/1995 | Friedman et al. | 424/450 |
| 5,633,226 A | 5/1997 | Owen et al. | 514/2 |
| 5,646,109 A | 7/1997 | Owen et al. | 514/2 |
| 5,658,898 A | 8/1997 | Weder et al. | 514/211 |
| 5,688,761 A | 11/1997 | Owen et al. | 514/2 |
| 5,997,888 A | 12/1999 | Weder et al. | 424/401 |
| 6,028,067 A | 2/2000 | Hong et al. | 514/200 |
| 6,245,349 B1 | 6/2001 | Yiv et al. | 424/450 |

FOREIGN PATENT DOCUMENTS

| | | | |
|---|---|---|---|
| DE | 19522693 | | 1/1997 |
| EP | 0082437 | | 6/1983 |
| EP | 0280394 | | 8/1988 |
| EP | 0 349 150 | * | 6/1989 |
| EP | 0349150 | | 3/1990 |
| EP | 0429248 | | 5/1991 |
| WO | 92/18147 | | 10/1992 |
| WO | 93/02664 | | 2/1993 |
| WO | 93/05767 | | 4/1993 |
| WO | 93/18752 | | 9/1993 |
| WO | 94/26252 | | 11/1994 |
| WO | 95/16441 | | 6/1995 |
| WO | 96/13273 | | 5/1996 |
| WO | 96/37192 | | 11/1996 |
| WO | 97/21428 | | 6/1997 |

OTHER PUBLICATIONS

Abstract for EP 0082437, Publication date Jun. 29, 1983.
Abstract for DE 19522693, Publication date Jan. 2, 1997.
CTFA On-Line, Sorbitan Derivative (Jul. 1, 2005).
Wade, Jr., L.G., Organic Chemistry, $2^{nd}$ edition, p. 1059, (1991).
POE Sorbitan Oleate EO 20, www.chemicalland21.com/arokorhi/specialychem/perchem/polyoxyethylene%20SOR, 3/3, last visited May 10, 2005.
Van Nostrand's Scientific Encyclopedia, Sixth Edition, vol. 1, p. 514, (1982).
Glossary of Chemical Terms, Hampel and Hawley, p. 48, (1976).

* cited by examiner

*Primary Examiner*—Gollamudi S Kishore
(74) *Attorney, Agent, or Firm*—Shiela A. Loggins

(57) ABSTRACT

A nanodispersion comprises
(a) a membrane-forming molecule,
(b) a coemulsifier and
(c) a lipophilic component,
in pharmaceutical end formulations, the nanodispersion being obtainable by
(α) mixing the components (a), (b) and (c) until a homogeneous clear liquid is obtained, and
(β) adding the liquid obtained in step (α) to the water phase of the pharmaceutical end formulations, where steps (α) and (β) may be carried out without high energy mixing or homogenization.

The nanodispersions prepared according to this invention are suitable as transport vehicles for pharmaceutical active agents.

26 Claims, No Drawings

USE OF NANODISPERSIONS IN PHARMACEUTICAL END FORMULATIONS

This is a continuation-in-part of application Ser. No. 09/306,006 filed May 06, 1999 now U.S. Pat. No. 7,081,253.

The present invention relates to the use of nanodispersions in pharmaceutical end formulations, to pharmaceutical end formulations comprising said nanodispersions and to the different pharmaceutical uses of these end formulations.

Pharmaceutical end formulations are understood here to mean formulations which comprise, in addition to the basic substances responsible for forming the pharmaceutical formulation, other functional active agents. These are added to the pharmaceutical base formulations and can be used for the therapeutic treatment of the nervous system, endocrine system, cardiovascular system, respiratory tract, gastrointestinal tract, kidneys and efferent urinary tracts, locomotor apparatus, immunological system, skin and mucosae and for the treatment of infectious diseases.

In order for these substances to have an effect at the desired site, they must be transported to the respective site. To optimise their availability at the site of action, many active agents are applied by means of so-called carrier and transport vehicles (carrier systems), for example mixed micelles, liposomes or nanoemulsions (nanoparticles). Examples of such active agents are amphotericin (NeXstar, Sequus, TLC), daunorubicin (NeXstar), doxorubicin (Sequus), inactivated hepatitis A viruses (Berna), or econazol (Cilag). Applying these active agents by means of said carrier systems results in therapeutic advantages such as fewer side-effects or better vaccinal effect.

Surprisingly, it has now been found that so-called nanodispersions of suitable composition can enhance the effectivity of medicinal agents in pharmaceutical end formulations.

Accordingly, this invention relates to the use of a nanodispersion, which comprises
(a) a membrane-forming molecule,
(b) a coemulsifier and
(c) a lipophilic component, in pharmaceutical end formulations, the nanodispersion being obtainable by ($\alpha$) mixing the components (a), (b) and (c) until a homogeneous clear liquid is obtained (so-called nanodispersion prephase), and ($\beta$) adding the liquid obtained in step ($\alpha$) to the water phase of the pharmaceutical end formulations, steps ($\alpha$) and ($\beta$) being carried out without any additional supply of energy.

Step ($\alpha$) is usually carried out at room temperature, where necessary with heating and under normal pressure conditions. Mixing is carried out using standard stirring apparatus, for example propeller, angled paddle or magnetic agitators, and without using any special mechanical stirring aids.

Components (a), (b) and (c) (=step ($\alpha$)) are mixed in anhydrous medium, i.e. it is not necessary to add any water.

Step ($\beta$) is carried out by adding the liquid obtained in step ($\alpha$), the nanodispersion pre-phase, to the water phase of the pharmaceutical end formulations. The particular choice of components (a), (b) and (c) results directly in ultrafine, monodisperse nanodispersions. In this case it is possible to forego homogenisation via nozzle, rotor-stator or ultrasound homogenisers, which is usually carried out to convert coarsely disperse or at least heterodisperse systems to fine monodisperse systems. Step ($\beta$) is thus characterised by the absence of high shear or cavitation forces.

Step ($\beta$) is usually carried out at room temperature, which is the range of the respective oil/water phase inversion temperature (PIT).

The nanodispersions characterised by the process steps ($\alpha$) and ($\beta$) contain particles having an average diameter of <50 nm, typically of less than 30 nm. The distribution is monodisperse and obeys a Gaussian distribution.

It is preferred to use a nanodispersion, which contains,
(a) as membrane-forming molecules, substances which are suitable for forming so-called bilayers,
(b) as coemulsifiers, substances which preferably form O/W structures and,
(c) as lipophilic component, a lipophilic agent customarily used for pharmaceutical preparations.

The nanodispersion preferably contains as component (a) a phospholipid, a hydrated or partially hydrated phospholipid, a lysophospholipid, a ceramide, or mixtures of these compounds,

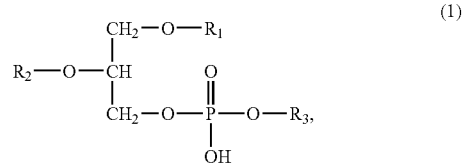

wherein
$R_1$ is $C_{10}$-$C_{20}$acyl;
$R_2$ is hydrogen or $C_{10}$-$C_{20}$acyl
$R_3$ is hydrogen, 2-trimethylamino-1-ethyl, 2-amino-1-ethyl; $C_1$-$C_5$alkyl which is unsubstituted or substituted by one or several carboxy, hydroxy or amino groups; the inositol or glyceryl group;

or salts of these compounds.

$C_{10}$-$C_{20}$Acyl is preferably straight-chain $C_{10}$-$C_{20}$alkanoyl containing an even number of carbon atoms and straight-chain $C_{10}$-$C_{20}$alkenoyl containing a double bond and an even number of carbon atoms.

Straight-chain $C_{10}$-$C_{20}$alkanoyl containing an even number of carbon atoms is, for example, n-dodecanoyl, n-tetradecanoyl, n-hexadecanoyl or n-octadecanoyl.

Straight-chain $C_{10}$-$C_{20}$alkenoyl containing a double bond and an even number of carbon atoms is, for example, 6-cis-or 6-trans-, 9-cis-or 9-trans-dodecenoyl, -tetradecenoyl, -hexadecenoyl, -octadecenoyl or -eicosenoyl, preferably 9-cis-octa-decenoyl (oleoyl), and also 9,12-cis-octadecadienoyl or 9,12,15-cis-octadecatrienoyl.

A phospholipid of formula (1), wherein $R_3$ is 2-trimethylamino-1-ethyl, is referred to by the trivial name lecithin, and a phospholipid of formula (1), wherein $R_3$ is 2-amino-1-ethyl, by the trivial name cephalin. Suitable are, for example, naturally occurring cephalin or lecithin, e.g. cephalin or lecithin from soybeans or chicken eggs with different or identical acyl groups, or mixtures thereof.

The phospholipid of formula (1) may also be of synthetic origin. The expression "synthetic phospholipid" is used to define phospholipids having uniform composition with respect to $R_1$ and $R_2$. Such synthetic phospholipids are preferably the lecithins and cephalins defined above, wherein the acyl groups $R_1$ and $R_2$ have a defined structure and which are derived from a defined fatty acid having a degree of purity greater than about 95%. $R_1$ and $R_2$ may be identical or different and unsaturated or saturated. Preferably, $R_1$ is saturated, for example n-hexadecanoyl, and $R_2$ is unsaturated, for example 9-cis-octadecenoyl (oleoyl).

The expression "naturally occurring" phospholipid defines a phospholipid that does not have a uniform composition with respect to $R_1$ and $R_2$. Such natural phospholipids are likewise lecithins and cephalins, wherein the acyl groups $R_1$ and $R_2$ are derived from naturally occurring fatty acid mixtures.

The requirement "substantially pure" phospholipid of formula (1) defines a degree of purity of more than 90% by weight, preferably of more than 95% by weight of the phospholipid of formula (1), which can be demonstrated by means of suitable determination methods, for example by paper chromatography, thin-layer chromatography, by HPLC or by means of enzymatic colour testing.

In a phospholipid of formula (1), $R_3$ defined as $C_1$-$C_4$alkyl is, for example, methyl or ethyl. Methyl is preferred.

$R_3$ defined as $C_1$-$C_5$alkyl substituted by one or several carboxy, hydroxy or amino groups is, for example, 2-hydroxyethyl, 2,3-dihydroxy-n-propyl, carboxymethyl, 1-or 2-carboxyethyl, dicarboxymethyl, 2-carboxy-2-hydroxyethyl or 3-carboxy-2,3-dihydroxy-n-propyl, 3-amino-3-carboxy-n-propyl or 2-amino-2-carboxy-n-propyl, preferably 2-amino-2-carboxyethyl.

Phospholipids of formula (1) containing these groups can be present in salt form, for example as sodium or potassium salt.

Phospholipids of formula (1), wherein $R_3$ is the inositol or glyceryl group, are known by the names phosphatidylinositol and phosphatidylglycerol.

The acyl radicals in the phospholipids of formula (1) are also customarily known by the names given in brackets:

9-cis-dodecenoyl (lauroleoyl), 9-cis-tetradecenoyl (myristoleoyl), 9-cis-hexadecenoyl (palmitoleoyl), 6-cis-octadecenoyl (petroseloyl), 6-trans-octadecenoyl (petroselaidoyl), 9-cis-octadecenoyl (oleoyl), 9-trans-octadecenoyl (elaidoyl), 9,12-cis-octadecadienoyl (linoleoyl), 9,12,15-cis-octadecatrienoyl (linolenoyl), 11-cis-octadecenoyl (vaccenoyl), 9-cis-eicosenoyl (gadoleoyl), 5,8,11,14-cis-eicosatetraenoyl (arachidonoyl), n-dodecanoyl (lauroyl), n-tetradecanoyl (myristoyl), n-hexadecanoyl (palmitoyl), n-octadecanoyl (stearoyl), n-eicosanoyl (arachidoyl), n-docosanoyl (behenoyl), n-tetracosanoyl (lignoceroyl).

A salt of the phospholipid of formula (1) is preferably pharmaceutically acceptable. Salts are defined by the existence of salt-forming groups in the substituent $R_3$ and by the free hydroxyl group at the phosphorus atom. The formation of internal salts is also possible. Alkali metal salts, especially the sodium salt, are preferred.

In a particularly preferred embodiment of this invention, purified lecithin from soybeans of the quality LIPOID S 100 or S 75, or a lecithin defined in the monograph USP23/NF 18, is used.

Component (a) is preferably used in a concentration of about 0.1 to 30% by weight, based on the total weight of components (a), (b) and (c).

Component (b) is preferably an emulsifier or emulsifier mixtures forming the preferred O/W structures.

Especially preferred emulsifiers are alkali, ammonium and amine salts of fatty acids. Examples of such salts are the lithium, sodium, potassium, ammonium, triethylamine, ethanolamine, diethanolamine or triethaolamine salts. It is preferred to use the sodium, potassium or ammonium (NR1R2R3) salts, wherein $R_1$, $R_1$ and $R_1$ are each independently of one another hydrogen, $C_1$-$C_4$lkyl or $C_1$-$C_4$hydroxyalkyl.

saturated and unsaturated alkyl sulfates, such as sodium docecylsulfate and alkane-sulfonates such as sodium dodecanesulfonate;

salts of colic acid, such as sodium cholate, sodium glycocholate and sodium taurocholate;

invert soaps (quats), such as zetylpyridinium chloride;

partial fatty acid esters of sorbitan, such as sorbitan monolaurate;

sugar esters of fatty acids, such as sucrose monolaurate;

alkylglucosides, such as n-octylglucoside or n-dodecylglucoside;

alkylmaltosides, such as n-dodecylmaltoside;

fatty acid partial glycerides, such as lauric acid monoglyceride;

$C_8$-$C_{18}$betaines, $C_8$-$C_{24}$alkylamido-$C_1$-$C_4$alkylenebetaines and $C_8$-$C_{18}$sulfobetaines;

proteins, such as casein;

polyglycerol esters of fatty acids;

propylene glycol esters of fatty acids;

lactates of fatty acids, such as sodium stearoyllactyl-2-lactate;

fatty alcohol phosphorates.

Emulsifiers of the polyoxyethylene type are very particularly preferred. Examples of such emulsifiers are:

polyethoxylated sorbitan fatty acid esters, such as polysorbate 80;

polyethoxylated fatty alcohols, such as oleth-20;

polyethoxylated fatty acids, such as polyoxyl 20 stearate;

polyethoxylated vitamin E derivatives, such as vitamin E polyethylene glycol 1000 succinate;

polyethoxylated lanoline and lanoline derivatives, such as laneth-20;

polyethoxylated fatty acid partial glycerides, such as diethylene glycol monostearate;

polyethoxylated alkylphenols, such as ethylphenolpoly(ethylene glycol ether)11;

sulfuric acid semiester polyethoxylated fatty alcohols and their salts, such as $C_{12}$-$C_{14}$-fatty alcohol ether sulfate-2 EO-sodium salt;

polyethoxylated fatty amines and fatty acid amides;

polyethoxylated carbon hydrates block polymers of ethylene oxide and propylene oxide, such as poloxamer 188.

Component (b) is present in the nanodispersion used according to this invention in a concentration of about 1 to about 50% by weight, based on the total weight of the components (a), (b) and (c).

Component (c) is preferably a natural or synthetic or a partially synthetic di-or triglyceride, a mineral oil, silicone oil, wax, fatty alcohol, guerbet alcohol or the ester thereof, a therapeutic oil, a lipophilic pharmaceutical active agent or a mixture of these substances.

Active agents suitable for pharmaceutical application are to be found, inter alia, in Arzneimittelkompendium 1997. Examples of suitable active agents are:

analgesics, antacids/ulcus treatments, antiallergic agents, antianemic drugs, antidepressants, antidiabetic agents, antidiarrheal agents, antidotes/addiction-combating agents/emetics, anti-emetics/antivertiginosa, antiepileptic agents, antihemorrhagic agents, anti-hypertensives, anti-hypotonic agents, antiinfectives, anticoagulants, antirheumatic agents/anti-inflammatory agents, appetite depressants, beta blockers, bronchodilators, cholinergic agents, dermatological agents, disinfectants, diagnostic agents, dietetic agents, diuretics, blood flow stimulants, gastroenterological agents, gout remedies, influenza remedies, gynecological agents, antihemorrhoidal agents, hormones, antitussives, hypnotics, immunological agents, intravenous infusions, cardiac remedies, contraceptives, contrast media, adrenocortical steroids, laxatives, liver and gall therapeutic agents, lipid metabolism preparations, local anesthetics, migraine analgesics, mineral metabolism preparations, muscle relaxants, narcotics, neuroleptic agents, odontological agents, ophthalmic agents, otorhinolaryngological agents (ORL), anti-parkinson drugs, psychostimulants, sedatives, spasmolytic agents, tonics/roborants, tranquilisers, anti-tuberculosis drugs, urological agents, preparations for varicose veins, consolidants and zytostatic agents.

Component (c) is present in the nanodispersions used according to this invention in a concentration of preferably 0.1 to 80% by weight, based on the total weight of components (a), (b) and (c).

The nanodispersion used according to this invention optionally comprises as facultative component (d) a solubiliser, preferably a $C_2$-$C_8$ alcohol, such as ethanol or propylene glycol.

A nanodispersion containing the components (a), (b), (c) and optionally (d) is distinguished by favourable phase properties of the solubilised functional pharmaceutical agent. Thus if there is opalescence and transparency in incident light, only a very slight turbidity shows that the dispersion is physically still different from the ideal state of a genuine molecular solution. Electron microscopic images show that a population of more than 98% is present in a Gaussian distribution as a suspension of particles (nanoparticles) having a particle size of less than about 50 nm, typically of less than about 30 nm. However, these distinctions from a genuine solution can be tolerated because of the particularly good homogeneity properties of the dispersion which can be evidenced, for example, by a surprisingly high storage stability, e.g. no separation after storing for several months at temperatures of up to room temperature (stability to be expected by extrapolation: more than two years).

Laser light scattering measurements and electron microscopic analysis (Cryo-TEM) confirm the very small size and excellent homogeneity of the nanoparticles present in the nanodispersion.

Another advantage of the nanodispersions used according to this invention is that they are easy to prepare.

The nanodispersions characterised by claim 1 are used according to this invention for pharmaceutic end formulations.

This invention also relates to the so-called nanodispersion prephase characterised in step ($\alpha$), which is obtainable by mixing the components (a) membrane-forming molecules,
(b) coemulsifier,
(c) lipophilic component and, optionally,
(d) a $C_2$-$C_8$ alcohol, preferably propylene glycol and, more preferably, ethanol until a homogeneous clear liquid is obtained, mixing being carried out in anhydrous medium.

In accordance with this invention, the nanodispersion prephase or the nanodispersion is used directly for pharmaceutical end formulations.

The pharmaceutical end formulations are preferably liquid, semisolid or solid preparations.

Examples of liquid pharmaceutical end formulations are injectable solutions, infusion solutions, drops, sprays, aerosols, emulsions, lotions, suspensions, drinking solutions, gargles and inhalants.

Examples of semisolid pharmaceutical end formulations are ointments, creams (O/W emulsions), rich creams (W/O emulsions), gels, lotions, foams, pastes, suspensions, ovula, plasters, including transdermal systems.

Examples of solid pharmaceutical end formulations are tablets, coated tablets, capsules, granules, effervescent granules, effervescent tablets, lozenges, sucking and chewing tablets, suppositories, implants, lyophilisates, adsorbates or powders.

This invention also relates to these end formulations.

The end formulations contain the nanodispersion in a concentration of 0.01 to 100 by weight, preferably of 0.05 to 20 by weight and, more preferably, of 0.1 to 10% by weight.

To prepare liquid and semisolid pharmaceutical end products (Examples 20 to 29), the nanodispersions are incorporated into the aqueous component of the end product. It is also possible to add instead of the nanodispersion the corresponding nanodispersion prephase to the water phase of the pharmaceutical end formulation. The nanodispersion prephase is added to the water phase with stirring and preferably at a temperature in the range of the respective oil/water phase inversion temperature (PIT).

Solid pharmaceutical end products, such as tablets (Example 30), effervescent tablets, coated tablets, granules, effervescent granules and plasters, are coated or loaded with nanodispersions by spraying or drenching. In certain cases it is advantageous to admix the dehydrated form of the nanodispersion to the solid mixture. The nanodispersion is usually dehydrated by freeze-or spray-drying in the presence of customary excipients. Capsules, in particular elastic gelatin capsules, can also be loaded with the nanodispersion prephase (Example 31).

Matrix-or membrane-controlled pharmaceutical application systems, such as oros capsules, transdermal systems, injectable microcapsules or implants, are loaded by conventional methods with nanodispersions. Oros capsules can also be loaded with the nanodispersion prephase.

In addition to the excipients for providing the pharmaceutical dosage form, the pharmaceutical end formulation can also contain other components, for example stabilisers, preservatives such as parabenes, antioxidants, and aromatics, fragrances or colourants.

The pharmaceutical end formulations are preferably used for the therapeutic treatment of the nervous system, endocrine system, cardiovascular system, respiratory tract, gastro-intestinal tract, kidneys and efferent urinary tracts, locomotor apparatus, immunological system, skin and mucosae as well as for the treatment of infectious diseases, tumours and vitamin and mineral deficiency diseases.

The novel pharmaceutical end formulation is preferably applied epicutaneously, buccally, lingually, sublingually, enterally (=perorally), rectally, nasally, pulmonally, per inhalationem, conjunctivally, intravaginally, intraurethrally, intracardially, intraarterially, intravenously, intralumbally, intrathecally, intraarticularly, intracutaneously, subcutaneously, intramuscularly and intraperitoneally.

In the following Examples, percentages are by weight. Unless otherwise stated, amounts of compounds used are based on the pure substance.

Working Examples for Nanodispersion Prephases

EXAMPLE 1

Miglyol 812 Nanodispersion Prephase

| | |
|---|---|
| soybean lecithin | 17.30% |
| polysorbate 80 | 34.00% |
| miglyol 812 | 34.50% |
| ethanol | 14.20% |

Preparation: Miglyol 812 and polysorbate 80 are mixed. The soybean lecithin is dissolved in ethanol and added to this mixture, resulting in a homogeneous clear liquid.

EXAMPLE 2

Miglyol 812 Nanodispersion Prephase

| | |
|---|---|
| soybean lecithin | 17.30% |
| oleth-20 | 34.00% |
| miglyol 812 | 34.50% |
| ethanol | 14.20% |

Preparation: Miglyol 812 and oleth-20 are mixed, with heating. The soybean lecithin is dissolved in ethanol and added to this mixture, resulting in a homogeneous clear liquid.

EXAMPLE 3

Miglyol 812 Nanodispersion Prephase

| | |
|---|---|
| soybean lecithin | 17.30% |
| laneth-20 | 34.00% |
| miglyol 812 | 34.50% |
| ethanol | 14.20% |

Preparation: Miglyol 812 and Laneth-20 are mixed, with heating. The soybean lecithin is dissolved in ethanol and added to this mixture, resulting in a homogeneous clear liquid.

EXAMPLE 4

Miglyol 812 Nanodispersion Prephase

| | |
|---|---|
| soybean lecithin | 17.30% |
| vitamin E polyethylene glycol succinate (vitamin E TPGS, Eastman) | 34.00% |
| miglyol 812 | 34.50% |
| ethanol | 14.20% |

Preparation: Miglyol 812 and vitamin E polyethylene glycol succinates are mixed, with heating. The soybean lecithin is dissolved in ethanol and added to this mixture, resulting in a homogeneous clear liquid.

EXAMPLE 5

Vitamin E Acetate Nanodispersion Prephase

| | |
|---|---|
| soybean lecithin | 9.00% |
| polysorbate 80 | 34.00% |
| vitamin E acetate | 36.60% |
| miglyol 812 | 13.00% |
| ethanol | 7.40% |

Preparation: Miglyol 812, vitamin E acetate and polysorbate 80 are mixed. The soybean lecithin is dissolved in ethanol and added to this mixture, resulting in a homogeneous clear liquid.

EXAMPLE 6

Vitamin A Palmitate Nanodispersion Prephase

| | |
|---|---|
| soybean lecithin | 17.30% |
| polysorbate 80 | 34.00% |
| vitamin A palmitate ($1.7 \times 10^6$ IU/g) | 4.50% |
| miglyol 812 | 30.00% |
| ethanol | 14.20% |

Preparation: Vitamin A palmitate, miglyol 812 and polysorbate 80 are mixed. The soybean lecithin is dissolved in ethanol and added to this mixture, resulting in a homogeneous clear liquid.

EXAMPLE 7

Tridecyl Salicylate Nanodispersion Prephase

| | |
|---|---|
| soybean lecithin | 11.00% |
| polysorbate 80 | 26.00% |
| tridecyl salicylate | 40.50% |
| miglyol 812 | 13.50% |
| ethanol | 9.00% |

Preparation: Tridecyl salicylate, miglyol 812 and polysorbate 80 are mixed. The soybean lecithin is dissolved in ethanol and added to this mixture, resulting in a homogeneous clear liquid.

Working Examples for Nanodispersions

EXAMPLE 8

Miglyol 812 Nanodispersion

| | |
|---|---|
| soybean lecithin | 1.73% |
| polysorbate 80 | 3.40% |

-continued

| | |
|---|---|
| miglyol 812 | 3.45% |
| ethanol | 1.42% |
| 10 mm phosphate buffer, pH 6 | ad 100.00% |

Preparation: The water phase (e.g. 90 kg) is placed, with stirring (e.g. magnetic agitator), at 50° C. in a vessel. The liquid nanodispersion prephase of Example 1 (e.g. 10 kg) is added to the water phase with stirring (e.g. with a magnetic agitator).

EXAMPLE 9

Miglyol 812 Nanodispersion

| | |
|---|---|
| soybean lecithin | 1.73% |
| oleth-20 | 3.40% |
| miglyol 812 | 3.45% |
| ethanol | 1.42% |
| 10 mm phosphate buffer, pH 6 | ad 100.00% |

The nanodispersion is prepared in analogy to the procedure of Example 8.

EXAMPLE 10

Migylol 812 Nanodispersion

| | |
|---|---|
| soybean lecithin | 1.73% |
| laneth-20 | 3.40% |
| miglyol 812 | 3.45% |
| ethanol | 1.42% |
| 10 mm phosphate buffer, pH 6 | ad 100.00% |

The nanodispersion is prepared in analogy to the procedure of Example 8.

EXAMPLE 11

Miglyol 812 Nanodispersion

| | |
|---|---|
| soybean lecithin | 1.73% |
| vitamin E polyethylene glycol succinate (vitamin E TPGS, Eastman) | 3.40% |
| miglyol 812 | 3.45% |
| ethanol | 1.42% |
| 10 mm phosphate buffer, pH 6 | ad 100.00% |

The nanodispersion is prepared in analogy to the procedure of Example 8.

EXAMPLE 12

Dexpanthenol Nanodispersion

| | |
|---|---|
| dexpanthenol | 5.00% |
| soybean lecithin | 1.73% |
| polysorbate 80 | 3.40% |
| miglyol 812 | 3.45% |
| ethanol | 1.42% |
| 10 mm phosphate buffer, pH 6 | ad 100.00% |

Preparation: The water phase comprising dexpanthenol (e.g. 90 kg) is placed, with stirring (e.g. magnetic agitator), at 50° C. in a vessel. The liquid nanodispersion prephase of Example 1 (e.g. 10 kg) is added to the water phase with stirring (e.g. magnetic agitator).

EXAMPLE 13

Dexpanthenol Nanodispersion

| | |
|---|---|
| dexpanthenol | 5.00% |
| soybean lecithin | 1.73% |
| polysorbate 80 | 3.40% |
| miglyol 812 | 3.45% |
| ethanol | 1.42% |
| 10 mm phosphate buffer, pH 7.4 | ad 100.00% |

The nanodispersion is prepared in analogy to the procedure of Example 12.

EXAMPLE 14

Vitamin E Acetate Nanodispersion

| | |
|---|---|
| vitamin E acetate | 2.00% |
| soybean lecithin | 0.49% |
| polysorbate 80 | 1.86% |
| miglyol 812 | 0.71% |
| ethanol | 0.63% |
| 10 mm phosphate buffer, pH 6 | ad 100.00% |

Preparation: The water phase (e.g. 94.54 kg) is placed, with stirring (e.g. magnetic agitator), at 50° C. in a vessel. The liquid nanodispersion prephase of Example 5 (e.g. 5.46 kg) is added to the water phase with stirring (e.g. magnetic agitator).

EXAMPLE 15

Vitamin E Acetate Nanodispersion

| | |
|---|---|
| vitamin E acetate | 2.00% |
| soybean lecithin | 0.49% |
| polysorbate 80 | 1.86% |
| miglyol 812 | 0.71% |

| | |
|---|---|
| ethanol | 0.63% |
| 10 mm phosphate buffer, pH 7.4 | ad 100.00% |

The nanodispersion is prepared in analogy to the procedure of Example 14.

EXAMPLE 16

Vitamin A Palmitate Nanodispersion

| | |
|---|---|
| vitamin A palmitate ($1.7 \times 10^6$ IU/g) | 0.45% |
| soybean lecithin | 1.73% |
| miglyol 812 | 3.00% |
| polysorbate 80 | 3.40% |
| ethanol | 1.42% |
| 10 mm phosphate buffer, pH 6 | ad 100.00% |

The nanodispersion is prepared in analogy to the procedure of Example 8.

EXAMPLE 17

Vitamin A Palmitate Nanodispersion

| | |
|---|---|
| vitamin A palmitate ($1.7 \times 10^6$ IU/g) | 0.45% |
| soybean lecithin | 1.73% |
| miglyol 812 | 3.00% |
| polysorbate 80 | 3.40% |
| ethanol | 1.42% |
| 10 mm phosphate buffer, pH 7.4 | ad 100.00% |

The nanodispersion is prepared in analogy to the procedure of Example 8.

EXAMPLE 18

Solcoseryl Nanodispersion

| | |
|---|---|
| solcoseryl | 1.00% |
| soybean lecithin | 1.73% |
| polysorbate 80 | 3.40% |
| miglyol 812 | 3.45% |
| ethanol | 1.42% |
| 10 mm phosphate buffer, pH 6 | ad 100.00% |

Preparation: The water phase comprising solcoseryl (e.g. 90 kg) is placed, with stirring (e.g. magnetic agitator), at 50° C. in a vessel. The liquid nanodispersion prephase of Example 1 (e.g. 10 kg) is added to the water phase with stirring (e.g. magnetic agitator).

EXAMPLE 19

Tridecyl Salicylate Nanodispersion

| | |
|---|---|
| tridecyl salicylate | 4.05% |
| soybean lecithin | 1.10% |
| polysorbate 80 | 2.60% |
| miglyol 812 | 1.35% |
| ethanol | 0.90% |
| 10 mm phosphate buffer, pH 6 | ad 100.00% |

Preparation: The water phase (e.g. 90 kg) is placed, with stirring (e.g. magnetic agitator), at 50° C. in a vessel. The liquid nanodispersion prephase of Example 7 (e.g. 10 kg) is added to the water phase with stirring (e.g. magnetic agitator).

The particle sizes and particle size distributions of nanodispersions are compiled in the following Table 1.

TABLE 1

| Nanodispersion | Particle diameter[1] [nm] | Standard deviation [nm] | Particle size distribution |
|---|---|---|---|
| migylol 812 nanodispersion Example 8 | 13.8 | 4.1 | Gauss |
| dexpanthenol nanodispersion Example 12 | 19.7 | 5.4 | Gauss |
| vitamin E acetate nanodispersion Example 14 | 12.2 | 5.5 | Gauss |
| vitamin A palmitate nanodispersion Example 16 | 10.1 | 3.9 | Gauss |
| solcoseryl nanodispersion Example 18 | 7.3 | 3.4 | Gauss |
| tridecyl salicylate nanodispersion Example 19 | 16.3 | 6.6 | Gauss |

As the following Tables show, nanodispersions also have excellent storage stability:
[1]The particle diameters and particle size distributions are determined via laser light scattering (Nicomp 370 Submicron Particle Sizer, number weighting)

Dexpanthenol Nanodispersion (Example 12)

TABLE 2

| Storage conditions | | | | Standard | |
|---|---|---|---|---|---|
| Duration [months] | Temperature [° C.] | pH | Diameter[2] [nm] | deviation [nm] | Dexpanthenol[3] content [%] |
| 0 | | 6.1 | 19.7 | 5.4 | 5.37 |
| 3 | 7 | 6.1 | 19.0 | 6.7 | 5.36 |
| | 25 | 6.1 | 22.2 | 7.7 | 5.32 |
| | 40 | 6.3 | 36.6 | 14.2 | 5.23 |
| 6 | 7 | 6.1 | 20.8 | 7.3 | 5.30 |
| | 25 | 6.2 | 24.1 | 9.2 | 5.26 |
| | 40 | 6.4 | 35.4 | 17.7 | 5.20 |

[2]The particle diameters and particle size distributions are determined via laser light scattering (Nicomp 370 Submicron Particle Sizer, volume weighting)
[3]The dexpanthenol content is determined via HPLC Vitamin E Acetate Nanodispersion (Example 14)

TABLE 3

| Storage conditions | | | Diameter[4] [nm] | Standard deviation [%] | Vitamin E acetate[5] content [%] |
|---|---|---|---|---|---|
| Duration [months] | Temperature [° C.] | pH | | | |
| 0 | | 6.1 | 12.2 | 5.5 | 2.04 |
| 3 | 7 | 6.1 | 16.1 | 6.6 | 2.02 |
| | 25 | 6.1 | 17.5 | 7.0 | 2.04 |
| | 40 | 6.0 | 15.4 | 6.8 | 2.01 |
| 6 | 7 | 6.1 | 17.0 | 6.9 | 2.04 |
| | 25 | 6.0 | 17.6 | 7.2 | 2.03 |
| | 40 | 6.0 | 20.8 | 7.9 | 2.02 |

[4] The particle diameters and the particle size distributions are determined via laser light scattering

[5] The vitamin E acetate content is determined via HPLC

Working Examples for Pharmaceutical End Formulations with Nanodispersions or Nanodispersion Prephases

EXAMPLE 20

Dexpanthenol 5% Controlled Dosage Non-Aerosol Spray

| Nanodispersion according to Example 12 | 100.00% |
|---|---|

The preparation has good anti-inflammatory action.

EXAMPLE 21

Dexpenthanol Vitamin E Acetate Lotion

| cera emulsificans cetomacrogolis | 3.0% |
|---|---|
| oleylium oleinicum | 6.0% |
| propylene glycolum | 3.0% |
| nanodispersion of Example 12 | 10.0% |
| nanodispersion of Example 14 | 10.0% |
| aqua purificata | ad 100.0% |

The preparation has good anti-inflammatory action.

EXAMPLE 22

Dexpanthenol 2.5% Eye Drops

| mannitol | 4.70% |
|---|---|
| nanodispersion of Example 13 | 50.00% |
| 10 mm phosphate buffer, pH 7.4 | ad 100.00% |

The preparation has good anti-inflammatory action.

EXAMPLE 23

Vitamin A Palmitate 0.1% Cream

| cetyl alcohol | 10.00% |
|---|---|
| hydrogenated groundnut oil | 20.00% |
| polysorbate 60 | 5.00% |
| propylene glycol | 20.00% |
| phenoxyethanol | 0.50% |
| nanodispersion of Example 16 | 23.00% |
| aqua purificata | ad 100.00% |

The preparation has good vitamin A action.

EXAMPLE 24

Vitamin A Palmitate 0.1% Aerosol

| sodium EDTA | 0.05% |
|---|---|
| mannitol | 4.70% |
| nanodispersion of Example 17 | 23.00% |
| 10 mm phosphate buffer, pH 7.4 | ad 100.00% |

The preparation has good vitamin A action.

EXAMPLE 25

Tridecyl Salicylate 1.0% Ointment

| citric acid | 0.75% |
|---|---|
| ammonia solution | 0.09% |
| medium-chain triglyceride | 5.00% |
| unguentum alcoholum lanae aquosum DAB 9 | 40.00% |
| nanodispersion of Example 19 | 25.00% |
| aqua purificata | ad 100.00% |

The preparation has good keratinolytic action.

EXAMPLE 26

Solcoseryl 0.5% Hydrogel

| sodium carboxymethylcellulose 450 cP | 3.50% |
|---|---|
| nanodispersion of Example 18 | 50.00% |
| aqua purificata | ad 100.00% |

The preparation is pleasantly cooling and has good antiphlogistic action.

EXAMPLE 27

Solcoseryl 1.0% Controlled Dosage Non-Aerosol Spray

| | |
|---|---|
| Nanodispersion of Example 18 | 100.00% |

The preparation has good anti-inflammatory action.

EXAMPLE 28

Vitamin E Acetate Drink Ampoules

| | |
|---|---|
| citric acid | 0.40% |
| glucose | 7.50% |
| aroma | 0.50% |
| nanodispersion of Example 14 | 50.00% |
| aqua purificata | ad 100.00% |

The preparation has good antioxidative action.

EXAMPLE 29

Vitamin E Acetate Injectable Solution

| | |
|---|---|
| mannitol | 4.70% |
| nanodispersion of Example 15 | 75.00% |
| 10 mm phosphate buffer, pH 7.4 | ad 100.00% |

The preparation has good antioxidative action.

EXAMPLE 30

Vitamin E Acetate Tablets

| | |
|---|---|
| Hydroxypropylmethylcellulose (methocel E4M CR grade) | 15.00% |
| magnesium stearate | 0.70% |
| vitamin E acetate[6] | 1.00% |
| lactose | ad 100.00% |

[6]Vitamin E acetate is incorporated during granulation in the form of the nanodispersion, i.e. the nanodispersion of Example 14 is used as granulating liquid.

The preparation has good antioxidative action.

EXAMPLE 31

Vitamin E Acetate Elastic Gelatin Capsules

Elastic gelatin capsules are filled with the nanodispersion prephase of Example 5. The preparation has good antioxidative action.

What is claimed is:

1. A method of preparing a pharmaceutical formulation of a lipophilic pharmaceutical active agent in the form of an oil-in-water nanodispersion, which comprises
   (α) preparing a nanodispersion prephase by mixing
   (a) 0.1 to 30% by weight of a phospholipid,
   (b) 1 to 50% by weight of a polyoxyethylene coemulsifier selected from the group consisting of polyethoxylated fatty alcohols, polyethoxylated fatty acids, polyethoxylated vitamin E derivatives, polyethoxylated lanoline and lanoline derivatives, and polyethoxylated fatty acid glycerides,
   (c) a lipophilic component comprising a natural or synthetic or a partially synthetic $C_4$-$C_{18}$ triglyceride, and
   (d) 3 to 30% by weight of ethanol,
   until a homogeneous clear liquid is obtained, and
   (β) adding the liquid obtained in step (α) to a water phase, where
   component (c) used in step (α), or the water phase in step (β), or both, additionally contain a lipophilic pharmaceutically active agent, where the total weight of lipophilic pharmaceutically active agent and $C_4$-$C_{18}$ triglyceride of component (c) ranges from 20 to 70% by weight, and where percentages relate to sum of the weight of the components (a), (b), (c), (d) and the lipophilic pharmaceutically active agent.

2. A method according to claim 1, wherein step (α) consists essentially of mixing of
   (a) 2 to 20% by weight of the phospholipid,
   (b) 15 to 50% by weight of the polyoxyethylene coemulsifier,
   (c) the lipophilic component consisting of the $C_4$-$C_{18}$ triglyceride and, optionally, the lipophilic pharmaceutically active agent, and
   (d) 3 to 30% by weight of ethanol.

3. A method according to claim 1, wherein step (β) is carried out in the absence of high shear or cavitation forces.

4. A method according to claim 1, wherein the particles in the nanodispersion have an average diameter of less than 50 nm.

5. A method according to claim 4, wherein the average particle diameter obtained is less than 30 nm.

6. A method according to claim 1, wherein essentially no water is added during step (α), which step essentially consists of the mixing of components (a), (b), (c) and (d).

7. A method according to claim 4, wherein step (β) is carried out without homogenisation.

8. A method according to claim 1, wherein the water phase is pure water or water containing a pharmaceutically active agent or up to 20% by weight of formulation aids and/or salts or both.

9. A method according to claim 1, wherein 1 part by weight of the nanodispersion prephase is added to 5 to 100 parts by weight of the water phase.

10. A method according to claim 2, wherein the total weight of the lipophilic pharmaceutically active agent is contained in component (c) added in step (α).

11. A method according to claim 1, wherein component (a) is lecithin, and the lipophilic pharmaceutically active agent is selected from the group consisting of sunscreens and fat-soluble vitamins.

12. A method of preparing a pharmaceutical formulation of a lipophilic pharmaceutical active agent in the form of an oil-in-water nanodispersion, which comprises (α) preparing a nanodispersion prephase by mixing
(a) 2 to 20% by weight of a phospholipid,
(b) 15 to 50% by weight of a polyoxyethylene coemulsifier selected from the group consisting of polyethoxylated sorbitan fatty acid esters, polyethoxylated fatty alcohols, polyethoxylated fatty acids, polyethoxylated vitamin E derivatives, polyethoxylated lanolin and lanolin derivatives, polyethoxylated fatty acid glycerides, polyethoxylated alkylphenols, sulfuric acid semiesters, polyethoxylated fatty alcohols and their salts, polyethoxylated fatty amines and fatty acid amides, and polyethoxylated carbohydrates,
(c) a lipophilic component comprising a natural or synthetic or a partially synthetic $C_4$-$C_{18}$triglyceride, and
(d) 3 to 30% by weight of ethanol,
until a homogeneous clear liquid is obtained, and
(β) adding the liquid prephase obtained in step (α) to a water phase, where component (c) used in step (α), or the water phase in step (β), or both, additionally contain a lipophilic pharmaceutically active agent, where the total weight of lipophilic pharmaceutically active agent and $C_4$-$C_{18}$triglyceride of component (c) ranges from 20 to 70% by weight, and the weight ratio of total lipophilic pharmaceutically active agent to $C_4$-$C_{18}$triglyceride of component (c) ranges from 1:3 to 5:1, and where percentages relate to sum of the weight of the components (a), (b), (c), (d) and the lipophilic pharmaceutically active agent.

13. A method according to claim 12, wherein step (α) comprises mixing of
(a) 5 to 20% by weight of the phospholipid,
(b) 15 to 40% by weight of the polyoxyethylene coemulsifier, and
where the total weight of lipophilic pharmaceutically active agent present in the nanodispersion and $C_4$-$C_{18}$triglyceride of component (c) ranges from 30 to 70% by weight.

14. A method according to claim 12, wherein none of steps (α) or (β) comprises addition of a sphingolipid or glycolipid.

15. A method according to claim 1, wherein component (b) in the nanodispersion is selected from the group consisting of polyethoxylated fatty alcohols, polyethoxylated fatty acids, polyethoxylated vitamin E derivatives, polyethoxylated lanolin and the derivatives thereof, polyethoxylated fatty acid glycerides.

16. A method according to claim 12 of preparing a pharmaceutical formulation of a lipophilic pharmaceutical active agent in the form of an oil-in-water nanodispersion, which method comprises (α) preparing a nanodispersion prephase by mixing
(a) 5.0 to 17.3% by weight of the phospholipid,
(b) 22.7 to 34.0% by weight of the polyoxyethylene coemulsifier,
(c) the lipophilic component, and
(d) 7.40 to 14.2% by weight of ethanol,
until a homogeneous clear liquid is obtained, and
(β) adding the liquid prephase obtained in step (α) to a water phase, where component (c) used in step (α), or the water phase in step (β), or both, additionally contain the lipophilic pharmaceutically active agent, where the total weight of lipophilic pharmaceutically active agent and $C_4$-$C_{18}$triglyceride of component (c) ranges from 47.6 to 56.3% by weight, and the weight ratio of total lipophilic pharmaceutically active agent to $C_4$-$C_{18}$triglyceride of component (c) ranges from 1.45:1 to 2.85:1.

17. A method of preparing a pharmaceutical formulation of a lipophilic pharmaceutical active agent in the form of an aqueous nanodispersion, which steps consist essentially of
(α) mixing the components
(a) 0.1 to 30% by weight of a phospholipid,
(b) 1 to 50% by weight of a polyoxyethylene coemulsifier selected from the group consisting of polyethoxylated fatty alcohols, polyethoxylated fatty acids, polyethoxylated vitamin E derivatives, polyethoxylated lanoline and lanoline derivatives, and polyethoxylated fatty acid partial glycerides,
(c) 0.1 to 80% by weight of a lipophilic component consisting of a natural or synthetic or a partially synthetic $C_4$-$C_{18}$triglyceride and a lipophilic pharmaceutically active agent, in which any pharmaceutically active agent is lipophilic and is always present in component (c), and
(d) 7.40 to 14.2% by weight of ethanol,
with conventional stirring apparatus until a homogeneous clear liquid is obtained, and
(β) adding the liquid obtained in step (α) to a water phase, wherein step (β) is carried out in the absence of high shear or cavitation forces, and wherein the particles in the nanodispersion have an average diameter of <50 nm.

18. A method according to claim 17, wherein the average particle diameter is less than 30 nm.

19. A method according to claim 18, wherein the particles size follows a Gaussian distribution with at least 90% of the particles having a size from the range 1 to 30 nm.

20. A Method according to claim 1, which is characterised in that the pharmaceutical formulation is a liquid, semisolid or solid preparation.

21. A pharmaceutical formulation prepared using the method of claim 1, which is a liquid formulation in the form of an injectable solution, infusion solution, drops, spray, aerosol, emulsion, lotion, suspension, drinking solution, gargle or inhalant; or a semisolid formulation in the form of an ointment, cream (O/W emulsions), rich cream (W/O emulsions), gel, lotion, foam, paste, suspension, ovula or plaster; or a solid formulation in the form of a tablet, coated tablet, capsule, granules, effervescent granules, effervescent tablet, lozenge, sucking and chewing tablet, suppositories, implant, lyophilisate, adsorbate or powder; or a matrix- or membrane-controlled pharmaceutical application system in the form of an oros capsule, transdermal system, injectable microcapsule.

22. A pharmaceutical end formulation according to claim 21, wherein the nanodispersion is present in the aqueous phase.

23. A pharmaceutical end formulation according to claim 21, wherein the nanodispersion is present in the aqueous phase in a concentration of 0.01 to 100% by weight.

24. A nanodispersion prephase as obtained in step (α) of claim 1.

25. A nanodispersion prephase as obtained in step (α) of claim 12.

26. A nanodispersion prephase as obtained in step (α) of claim 17.

* * * * *